United States Patent [19]

Hermann et al.

[11] Patent Number: 5,756,867
[45] Date of Patent: May 26, 1998

[54] RECOVERY OF NITRIC ACID FROM NITRATION PROCESSES

[75] Inventors: Heinrich Hermann, Köln; Jürgen Gebauer, Troisdorf, both of Germany

[73] Assignee: Josef Meissner GmbH & Co., Köln, Germany

[21] Appl. No.: 529,100

[22] Filed: Sep. 15, 1995

[30] Foreign Application Priority Data

Apr. 4, 1995 [DE] Germany ............... 195 12 114.7

[51] Int. Cl.$^6$ ............................................. C07C 205/08
[52] U.S. Cl. ................................... 568/934; 568/932
[58] Field of Search ............................ 568/934, 932

[56] References Cited

U.S. PATENT DOCUMENTS 3,204,000  8/1965  Samuelsen et al. ............... 260/645
5,001,286  3/1991  Witt et al. ........................ 568/934

*Primary Examiner*—Gary Geist
*Assistant Examiner*—Sreeni Padmanabhan
*Attorney, Agent, or Firm*—Cohen, Pontani Lieberman & Pavane

[57] ABSTRACT

A process for the removal and recovery of nitric acid, sulphuric acid and nitrous oxide ($NO_x$) from crude dinitrotoluene (DNT) obtained by nitrating with a nitrating acid, a benzene derivative selected from the group consisting of tolulene or mononitrotoluene (after separation from the dinitrotoluene from the nitrating acid, wherein the crude dinitrotoluene is extracted in a plurality of steps whereby a dilute aqueous solution of nitric, sulfuric and nitrous acids countercurrently contacts the crude dinitrotoluene, the volume ratio of the dinitrotoluene to the aqueous solution being between 1:3 and 10:1, the extraction steps resulting in the formation of an aqueous extract which is blended directly into the nitrating acid for re-use in the acid nitration of the benzene derivative.

10 Claims, No Drawings

RECOVERY OF NITRIC ACID FROM NITRATION PROCESSES

BACKGROUND OF THE INVENTION

The present invention relates to a process for removal and recovery of nitric acid, sulfuric acid and nitrous oxides ($NO_x$) from the crude dinitrotoluenes (DNT) obtained during nitration of toluene or mononitrotoluene (MNT) after separation of the nitrating acid.

DNT is produced in a multi-step process countercurrently. During this process a constant excess of nitric acid of 1.01 to 1.08 of the quantity required in the nitrating acids is necessary in order to achieve a quantitative conversion of the materials (toluene or MNT) to be nitrated in the respective steps.

During the first nitration step (NIT step), at a temperature range of 35° to 45° C., toluene is selectively converted into MNT using the DNT spent acid coming from the DNT step fortified by fresh nitric acid. The nitrating acid (MNT spent acid) obtained after completion of the reaction in the first nitration step, still contains 70–72% sulfuric acid, approximately 0.3 to 0.7% nitric acid and 0.4 to 2.0% $NO_x$ as $HNO_2$ in equilibrium with the organic phase. After separation of the phases, the MNT spent acid is sent to MNT spent acid treatment to remove the residual quantity of nitric acid, $NO_x$ and the dissolved MNT/DNT.

The crude MNT, still containing nitrocresols, nitric acid, $NO_x$ and other decomposition products, is converted directly without purification into DNT in the second step with fresh mixed acid of 96% sulfuric acid and approximately 98% or 64 to 67% nitric acid. Beside the DNT-isomer mixture of 76% 2,4-DNT, 19.5% 2,6-DNT, 0.6% 2,5-DNT, 3.7% "Ortho-Isomers" (2,3- and 3,4-DNT) and 0.08% 3,5-DNT, max. 0.01% MNT and traces of TNT (e.g. 0.02%), the crude DNT obtained after separation of the nitrating acid (DNT spent acid) still contains nitrocresols, nitric acid, sulfuric acid and dissolved nitrogen dioxide ($NO_2$) (refer to U.S. Pat. No. 4,482,769). The amount of nitric acid, sulfuric acid and $NO_x$ diluted and suspended in the crude DNT depends on the composition of the DNT spent acid and the quality of phase separation of the DNT spent acid from the crude DNT after conversion has been completed. To remove these materials, the crude DNT is submitted to a washing process. The washing takes place at 60° to 70° C. in three steps. All acids (as sulfuric acid, nitric acid, $NO_x$) are extracted with water in the first step (acid washing). In the second washing step (alkaline washing) all weakly acidic materials as e.g. nitrocresols are extracted with sodium carbonate solutions. During the third and last washing step the traces of sodium carbonate and cresols are removed with water.

DESCRIPTION OF THE PRIOR ART

The mixed waste waters saturated with DNT and coming from the washing are always acidic due to the high content of acids in the crude DNT and—depending of the amount of washing water (1.5 to 3 m³/DNT)—contain approximately 0.2 to 3% sulfuric acid, 1 to 3% nitric acid, 0.1 to 0.2% $HNO_2$, 0.2 to 0.5% DNT (depending on temperature and acid content), 400 to 800 ppm nitrocresols and other decomposition products from oxidation of the nitrocresols in the DNT step.

In addition to the toxic nitrocresols which have to be removed before the waste water can be discharged into an outfall ditch the high content of nitric acid of 1 to 3% and sulfuric acid of 0.2 to 3% in the waste water also constitutes a problem. The nitric acid in the waste water as well as the residual nitric acid and the $NO_x$ in the spent acid are lost for the nitration process. Depending on the treatment methods for the spent acid they are obtained as a more or less weak nitric acid which cannot be returned to nitration directly.

Before discharging these waste waters from the acid washing of the DNT or from the treatment of the MNT spent acid in an outfall ditch, not only the diluted MNT/DNT but also the high content of nitrate and sulfate has to be reduced to the legally valid limit values for the discharge of waste waters (e.g. 50 mg/m³ for nitrate, 1200 mg for sulfate and CSB 175 mg $O_2$/l ). This is only possible by treating the waste water with calcium hydroxide so that the excessive sulfate is separated as calcium sulfate with a subsequent biological reduction of the nitrates and the organic load. To reduce the loss of nitric acid of approximately 8% in the amount required for nitration, and thus to reduce the processing work during removal of the nitric acid from the waste water, it was suggested to reconcentrate, e.g. the weak nitric acid of approximately 16.3% and approximately 4.9% $HNO_2$ obtained by flush evaporation of the MNT, spent acid to nitric acid of 65% by distillation. Said nitric acid—65% can be returned for nitration (EP-B-415 354).

Moreover, an attempt was made to recover nitric acid, sulfuric acid and $NO_x$ dissolved or suspended in the crude DNT by washing said crude DNT with up to 10% water so that the concentrated washing acid obtained during washing with a density that is higher than that of the DNT can be returned to nitration (EP-B-279 312). By this procedure about 50 to 72% of the nitric acid diluted in the crude DNT can be recovered. Still, the nitric acid amount of 0.3 to 0.6% (3–6 kg/t DNT) remaining in the DNT is introduced into the waste water via the washing and constitutes a considerable concentration.

To recover nitric acid from crude DNT it was further attempted (U.S. Pat. No. 4,257,986) to extract a part of the nitric acid contained in crude DNT by washing said crude DNT with a treated MNT spent acid and to subsequently return said MNT spent acid loaded with nitric acid for nitration again. With this procedure the nitric acid and $NO_x$ dissolved in the crude DNT cannot be recovered completely; they can only be extracted according to the distribution equilibrium for these acids between DNT and the spent acid (about 50–60% of the nitric acid dissolved in the DNT).

Furthermore, an attempt was made to reduce the losses of nitric acid—due to extraction with the crude DNT or the formation of $NO_x$ from nitric acid deriving from oxidation or the dinitrocresols contained in the crude MNT (mainly 2,4-dinitroparacresol)—by changing the nitration parameters. This is done by nitrating the toluene to MNT not at 70 to 72%, but at 72 to 76% sulfuric acid in the MNT spent acid (EP-B-155 586).

This nitration of toluene to MNT in a MNT spent acid having a sulfuric acid content of approximately 75% has the effect that up to 25% less dinitrocresol is formed compared to nitration in a MNT spent acid of 70% sulfuric acid (Hanson et al., ACS Symposium Series No. 22, 132 (1976) Industrial and Laboratory Nitration).

All these measures contribute to reducing losses of nitric acid during nitration of toluene to DNT. However, the washing of the crude DNT according to EP-B-279 312 as well as the reconcentration of the nitric acid obtained from the flush evaporation of MNT spent acid according to EP-B-415 354 result in a reduction of the nitric acid losses in the respective partial steps. These known measures are partial solutions for reducing the losses of nitric acid during nitration at the respective step but relating to the complete process (nitration, spent acid treatment, and washing) still waste waters with high concentrations of nitrate may be obtained from a DNT plant.

SUMMARY OF THE INVENTION

The invention is based on the objective to carry out washing of the crude DNT for the removal of the nitric acid, sulfuric acid and nitric oxides in such way that these acids can be recovered almost completely.

The process of the present invention relates to the removal and recovery of nitric acid, sulfuric acid and nitrous oxide ($NO_x$) from the crude dinitrotoluenes (DNT) obtained by nitrating with nitrating acids, a benzene derivative selected from the group consisting of toluene or mononitrotoluene (MNT) or a blend of both, after separation of said dinitrotoluenes from said nitrating acid. The crude dinitrotoluenes are extracted in a plurality of steps whereby a dilute aqueous solution of nitric, sulfuric and nitrous acids countercurrently contacts said crude dinitrotoluenes, with the volume ratios of said dinitrotoluenes to said aqueous solution being between 1:3 and 10:1. The extraction steps result in the formation of an aqueous extract which can be blended directly into said nitrating acid for re-use in the acid nitration of said benzene derivatives, or it can be blended with said nitrating acid after said aqueous extract is reconcentrated.

DESCRIPTION OF THE PREFERRED EMBODIMENTS

The subject of the invention is a process for removal and recovery of nitric acid, sulfuric acid and nitric oxides from the crude dinitrotoluenes obtained during nitration of toluenes and mononitrotoluenes, after the nitrating acid has been separated. With this process the nitric, sulfuric and nitrous acid are extracted from the crude dinitrotoluenes with a diluted aqueous solution of said acids in wherein two to four steps—countercurrently, wherein a volume ratio of the dinitrotoluenes to the diluted acidic extraction solution is 1:3 to 10:1, preferably 1:1 to 4:1, and the aqueous extract can be refed for nitration directly or after reconcentration.

In all extraction steps for the dinitrotoluene the working temperature is above the melting point of the dinitrotoluenes and the density of the aqueous solution should be different from, preferably lower than, the density of the dinitrotoluenes. The diluted acidic extraction solution of the acid mixture of sulfuric, nitric and nitrous acid is circulated within each extraction step. The desired volume ratio of the dinitrotoluenes to the aqueous solution of nitric, sulfuric and nitrous acid can be adjusted by feeding fresh water into the extraction cycle of the diluted aqueous solution of the last extraction step. Instead of fresh water, the condensate from the reconcentration of the diluted acidic extraction solution may be added. The aqueous solution extracted during the first extraction step is a nitric/sulfuric/nitrous acid mixture with 25 to 40% total acid. This total acid is reconcentrated alone or preferably together with the nitric acid obtained during the MNT spent acid treatment so that the total acid content is about 65%, calculated as $HNO_3$.

Is it surprising that with a process according to this invention the yield of nitric acid, $NO_x$ and sulfuric acid extractable from the crude DNT is 98% or higher. In general, a considerable amount of nitric acid will be re-extracted into the organic phase during the washing of crude DNT with a washing acid containing a nitric/sulfuric acid mixture with 25 to 40% total acid. Thus, from e.g. 25% by weight of nitric acid in equilibrium with the DNT at 60° C. such a quantity of nitric acid is re-extracted into the liquid DNT, that a DNT with approximately 0.6% nitric acid is obtained.

Furthermore, it is surprising that, when proceeding according to the invention the $NO_x$ ($NO_2$) dissolved in the crude DNT can be recovered as nitric acid almost completely, according to the equation $6NO_2 \leftrightharpoons 4HNO_3 + 2NO$. Consequently, the $NO_2$ is extracted from the DNT before the alkaline second washing step of the crude DNT, thus reducing the nitrate/nitrite concentration in the alkaline waste water to a minimum. The nitrogen monoxide is collected as usual and can also be reused for nitration after re-oxidation to nitric acid in the waste gas treatment.

The quantity of fresh water added in the last washing step of the acid washing of crude DNT depends not only on the selected acid concentration in the first washing step (e.g. 30% total acid as nitric acid), but also on the amount and the ratio of the nitric acid/sulfuric acid/$NO_2$ dissolved in the crude DNT.

In order to maintain the selected ratio of DNT to the acidic washing solution in the individual extraction steps, the separated diluted acid is fed back into the extraction step after separation of the phases and only the excess is transferred to the next extraction step.

The nitric acid/sulfuric acid mixture containing approximately 30 to 40% total acid that leaves the first extraction step at a temperature of 65° to 75° C. is saturated with DNT and can be transferred back into the nitration process either directly or after further reconcentration to an acid content of 65% total acid. Moreover, it can also be refed together with the mixture of weak nitric acid (15–30%) and MNT/DNT obtained during the stripping of MNT spent acid.

Another possibility is to reconcentrate the nitric/sulfuric acid mixture resulting from countercurrent extraction of the crude DNT together with the mixture of weak nitric acid and MNT/DNT obtained during stripping of MNT spent acid so that an acid mixture of sulfuric and nitric acid with a concentration of up to 65% total acid is obtained this blend can also be returned to nitration in the MNT step together with the MNT/DNT from the stripping of the MNT spent acid.

By these process steps not only is the concentration of nitrate and sulfate in the waste water reduced from approximately 1 to 3% to 200 to 500 ppm or approximately 20 to 25 kg of nitrate and nitrite/ton of DNT to 300 to 700 g of nitrite and nitrite/ton of DNT, but also the excess of nitric acid required for complete nitration in the individual nitration steps is in this way recovered and made usable for nitration.

According to the invention, the washing is carried out in several washing steps countercurrently. At least two washing steps are required to recover at least 95% of the $HNO_3$ and $NO_x$ dissolved in the DNT as nitric/sulfuric acid mixture of 30 to 40% total acid. Any device which is suitable for washing DNT countercurrently can be applied. Preferably, the washing should be performed in mixer/settlers, as described e.g. in DE-B-11 35 425.

The product quality of the crude DNT will neither be affected by feeding back the nitric/sulfuric acid mixture of 30 to 40% total acid directly or after reconcentration into nitration nor by feeding said acid mixture back together with the diluted nitric acid solution from the stripping of MNT spent acid directly or after reconcentration.

EXAMPLE

After separation from the DNT spent acid, 3400 kg/h of crude DNT are washed in the acid washing stage at a temperature above the melting point of the DNT/isomer mixture (60°–75° C.) in two extraction steps with diluted aqueous solutions of sulfuric, nitric and nitrous acid ($H_2SO_4/HNO_3/HNO_2$). An untreated crude DNT containing approximately 8.9 kg of sulfuric acid per ton of DNT, approx. 17.5 kg of nitric acid per ton and approximately 9.3 kg of nitrogen dioxide per ton is washed in the first extraction step with a washing acid composed of 6.25% sulfuric acid, 17.06% nitric acid and 0.42% $HNO_2$ in a volume ratio of 1:1 DNT : washing acid. Simultaneously, washing acid from the second extraction step having a lower acid concentration than in the first extraction step is fed in such quantity, that the concentration of the acid in the first extraction step is not changed.

Likewise, in the second extraction step washing is performed in the phase ratio 1:1 with a diluted nitric/sulfuric acid mixture having the same concentration as the washing acid which is transferred from the second washing step to the first one. At the same time a certain amount of fresh water is charged into the second extraction step so that the concentration of the acids in the washing acid is not changed by extracting the acid still dissolved after the first extraction order to step from the DNT.

In order to maintain the desired volume ratio of 1:1 in each washing step, the washing acid draining off the separation part of a mixer/settler after phase separation is returned to the washing part as washing acid as internal recycle.

The excess of washing acid in each extraction step obtained by permanently feeding weak washing acid from the previous extraction step or obtained at the last extractor by adding water is returned to the previous extraction step. Instead of water, also distillate (containing traces of $HNO_3$, $HNO_2$ and $H_2SO_4$) obtained from the reconcentration of washing acid from the first washing step can be fed.

The washing acid with a temperature of between 60° to 70° C. draining off from the first extraction step, containing 6.25% $H_2SO_4$, 17.06% $HNO_3$ and 0.42% $HNO_2$ total acid 23.73% by weight and being saturated with DNT/MNT, is either fed directly into nitration or said acid is reconcentrated separately or together with a condensate (consisting of approximately 20 to 30% $HNO_3$, approximately 0 to 2% sulfuric acid and a MNT/DNT mixture) from the stripping of MNT spent acid to an acid concentration of maximum 65% total acid, calculated as nitric acid, in a distilling device.

Said acid of maximum 65% total acid leaving the reconcentration is refed to nitration. The distillate obtained with approximately 0.3 to 0.5% acid, being mainly nitric acid, is returned to the extraction washing as washing acid.

After the last washing step, approximately 98% of the nitrogen-containing acids ($HNO_3$ and $HNO_2$ originally present in crude DNT) and 99% of the sulfuric acid have been extracted countercurrently into the washing acids of the acid washing stage and have thus been available for reuse in the nitration process.

We claim:

1. A process for the removal and recovery of nitric acid, sulfuric acid and nitrous oxide ($NO_x$) from the crude dinitrotoluene (DNT) obtained by nitrating with a nitrating acid, a benzene derivative selected from the group consisting of toluene or mononitrotoluene (MNT) after separation of said dinitrotoluene from said nitrating acid, wherein said crude dinitrotoluene is extracted in 2–4 steps whereby a dilute aqueous solution of nitric, sulfuric and nitrous acids countercurrently contacts said crude dinitrotoluene, said volume ratio of said dinitrotoluene to said aqueous solution being between 1:3 and 10:1, said extraction steps resulting in the formation of an aqueous extract which is blended directly into said nitrating acid for re-use in the acid nitration of said benzene derivative, the volume ratio being adjusted by feeding one of fresh water and condensate into the dilute aqueous solution in a last of the extraction steps.

2. The process defined in claim 1, wherein said aqueous extract is blended with said nitrating acid after said aqueous extract has been reconcentrated.

3. The process defined in claim 2, wherein said volume ratio of said dinitrotoluene to aqueous solution is between 1:1 and 4:1.

4. The process defined in claim 1, wherein said weak aqueous solution in each of said extraction steps is recirculated in a loop.

5. The process defined in claim 4, wherein said aqueous solution in all said steps possesses a density valve which is different from the density valve possessed by said dinitrotoluene.

6. The process defined in claim 5, wherein said density valve of said aqueous solution is lower than said density valve of said dinitrotoluene.

7. The process defined in claim 6, wherein said dinitrotoluene has a melting temperature and said extraction steps occur at a temperature above said melting temperature of said dinitrotoluene.

8. The process defined in claim 7, wherein said dilute aqueous solution of nitric, sulfuric and nitrous acids present after the first said extraction step is concentrated to a total acid content of 65%, calculated as $HNO_3$.

9. The process defined in claim 8, wherein mononitrotoluene is formed along with a mononitrotoluene spent acid after completion of the nitration reaction, and wherein said mononitrotoluene spent acid and said aqueous solution of nitric, sulfuric and nitrous acids present after the first said extraction step are blended and reconcentrated.

10. The process defined in claim 9, wherein said reconcentration of said dilute aqueous solution forms a condensate which is added to the extract resulting from the final extraction step.

* * * * *